US012691212B2

(12) United States Patent
Hanlon

(10) Patent No.: US 12,691,212 B2
(45) Date of Patent: Jul. 28, 2026

(54) SPOOL VALVE FOR BODY CAVITY IRRIGATION DEVICES

(71) Applicant: Hollister Incorporated, Libertyville, IL (US)

(72) Inventor: Matthew J. Hanlon, Durham, NC (US)

(73) Assignee: Hollister Incorporated, Libertyville, IL (US)

( * ) Notice: Subject to any disclaimer, the term of this patent is extended or adjusted under 35 U.S.C. 154(b) by 1266 days.

(21) Appl. No.: 17/617,849

(22) PCT Filed: Jun. 25, 2020

(86) PCT No.: PCT/US2020/039577
§ 371 (c)(1),
(2) Date: Dec. 9, 2021

(87) PCT Pub. No.: WO2021/025801
PCT Pub. Date: Feb. 11, 2021

(65) Prior Publication Data
US 2022/0233759 A1 Jul. 28, 2022

Related U.S. Application Data

(60) Provisional application No. 62/882,246, filed on Aug. 2, 2019.

(51) Int. Cl.
A61M 3/02 (2006.01)

(52) U.S. Cl.
CPC ........ A61M 3/0295 (2013.01); A61M 3/0258 (2013.01); A61M 3/0202 (2021.05)

(58) Field of Classification Search
CPC .............. A61M 3/0295; A61M 3/0258; A61M 3/0202; A61M 5/16827; A61B 1/00068
See application file for complete search history.

(56) References Cited

U.S. PATENT DOCUMENTS 1,004,103 A 9/1911 Tacey
1,286,083 A 11/1918 Pennington
(Continued)

FOREIGN PATENT DOCUMENTS

AT 369994 B 2/1983
CN 204395194 U 6/2015
(Continued)

OTHER PUBLICATIONS

Urinary Incontinence Applicance, Aids and Equipment, R.N.P. Carroll, retrieved on Apr. 3, 14 from http://link.springer.com/chapter/10.1007/978-1-4471-1461-1_6# dated Dec. 31, 1992.
(Continued)

*Primary Examiner* — Kai H Weng
*Assistant Examiner* — Katherine-Ph Minh Pham
(74) *Attorney, Agent, or Firm* — Cook Alex Ltd.

(57) ABSTRACT

A spool valve for use in a hydraulic control circuit of a trans-anal irrigation device, with the spool valve including a valve body having an elongated bore and a plurality of ports spaced apart along and in fluid communication with the bore, and a spool that is movable within the bore. An actuator moves the spool relative to the bore to provide a hydraulic control circuit that directs fluid in a tubing set to provide at least fluid communication alternatively between a reservoir and a retention balloon, between and the reservoir and a main passage through a catheter, and between the retention balloon and the reservoir.

13 Claims, 8 Drawing Sheets

(56)         References Cited

U.S. PATENT DOCUMENTS

| | | | |
|---|---|---|---|
| 1,710,701 A | 4/1929 | Hertzberg | |
| 1,853,202 A | 4/1932 | Catlin | |
| 2,691,373 A | 10/1954 | Bried | |
| 3,653,377 A | 4/1972 | Rebold | |
| 3,731,676 A | 5/1973 | Rebold | |
| 3,794,031 A | 2/1974 | Bloom | |
| 3,802,418 A | 4/1974 | Clayton | |
| 3,854,483 A | 12/1974 | Powers | |
| 3,889,676 A | 6/1975 | Greene | |
| 3,894,540 A | 7/1975 | Bonner, Jr. | |
| 3,910,274 A | 10/1975 | Nolan | |
| 3,934,722 A | 1/1976 | Goldberg | |
| 4,043,345 A | 8/1977 | Kramann et al. | |
| 4,109,659 A | 8/1978 | Sheridan | |
| 4,117,847 A | 10/1978 | Clayton | |
| 4,324,274 A * | 4/1982 | Golan | F16K 11/07 |
| | | | 137/625.68 |
| 4,386,607 A | 6/1983 | Miller | |
| 4,604,093 A * | 8/1986 | Brown | A61M 5/16827 |
| | | | 137/625.11 |
| 4,682,979 A | 7/1987 | Girouard | |
| 4,890,340 A | 1/1990 | Lovitt | |
| 4,956,298 A | 9/1990 | Diekmann | |
| 5,097,540 A | 3/1992 | Lovitt | |
| 5,149,326 A | 9/1992 | Woodgrift et al. | |
| 5,176,630 A | 1/1993 | Shilling et al. | |
| 5,190,519 A | 3/1993 | Mead et al. | |
| 5,217,114 A | 6/1993 | Gadberry et al. | |
| 5,225,165 A | 7/1993 | Perlman | |
| 5,405,319 A | 4/1995 | Abell | |
| 5,413,561 A | 5/1995 | Fischell et al. | |
| 5,417,326 A | 5/1995 | Winer | |
| 5,443,445 A | 8/1995 | Peters et al. | |
| 5,864,895 A | 2/1999 | Ota et al. | |
| 5,868,265 A | 2/1999 | Kobayashi | |
| 5,881,774 A | 3/1999 | Utterberg | |
| 6,106,506 A | 8/2000 | Abell et al. | |
| 6,125,843 A | 10/2000 | Gold et al. | |
| 6,258,078 B1 | 7/2001 | Thilly | |
| 6,468,245 B2 | 10/2002 | Alexandersen | |
| 6,585,721 B2 | 7/2003 | Fiore | |
| 6,641,002 B2 | 11/2003 | Gerenraich et al. | |
| 6,751,813 B2 | 6/2004 | Chung | |
| 6,761,702 B2 | 7/2004 | Smith | |
| 6,822,253 B1 | 11/2004 | Martin et al. | |
| 6,908,013 B2 | 6/2005 | Thomson et al. | |
| 6,984,226 B1 | 1/2006 | Abell | |
| 7,118,050 B1 | 10/2006 | Chen | |
| 7,120,487 B2 | 10/2006 | Nelson | |
| 7,147,627 B2 | 12/2006 | Kim et al. | |
| 7,237,729 B2 | 7/2007 | Chen | |
| 7,347,386 B2 | 3/2008 | Chen | |
| 7,438,704 B1 | 10/2008 | Kawashima et al. | |
| 7,477,835 B2 | 1/2009 | Yoo | |
| 7,546,931 B2 | 6/2009 | Giusti | |
| 7,571,804 B2 | 8/2009 | Kjellmann Bruun et al. | |
| 7,585,294 B2 | 9/2009 | Jensen et al. | |
| 7,614,514 B2 | 11/2009 | Fuchs | |
| 7,625,355 B2 | 12/2009 | Yu | |
| 7,682,353 B2 | 3/2010 | Tanghoj | |
| 7,717,284 B2 | 5/2010 | Giusti | |
| 7,748,550 B2 | 7/2010 | Cho | |
| 7,867,220 B2 | 1/2011 | Tanghoj | |
| 7,886,907 B2 | 2/2011 | Murray et al. | |
| 7,914,505 B2 | 3/2011 | Moeller-Jensen et al. | |
| 7,942,578 B2 | 5/2011 | Andersen | |
| 7,967,744 B2 | 6/2011 | Kaye et al. | |
| 8,137,309 B2 | 3/2012 | Nishtala et al. | |
| 8,172,101 B2 | 5/2012 | Giusti | |
| 8,181,778 B1 | 5/2012 | Van Groningen et al. | |
| 8,230,993 B2 | 7/2012 | Tanghoej | |
| 8,231,589 B2 | 7/2012 | Moeller-Jensen et al. | |
| 8,282,624 B2 | 10/2012 | Tanghoej et al. | |
| 8,361,057 B2 | 1/2013 | Tanghoej et al. | |
| 8,398,615 B2 | 3/2013 | Torstensen et al. | |
| 8,434,639 B2 | 5/2013 | Markert | |
| 8,439,213 B2 | 5/2013 | Goria et al. | |
| 8,448,798 B2 | 5/2013 | Groubert | |
| 8,491,568 B2 | 7/2013 | Schertiger et al. | |
| 8,518,012 B2 | 8/2013 | Smith | |
| 8,568,348 B2 | 10/2013 | Modaver et al. | |
| 8,574,206 B2 | 11/2013 | Bjerregaard et al. | |
| 8,579,115 B2 | 11/2013 | Murphy et al. | |
| 8,579,850 B2 | 11/2013 | Bjerregaard | |
| 8,657,801 B2 | 2/2014 | Nielsen et al. | |
| 8,752,722 B2 | 6/2014 | Kuhn et al. | |
| 8,863,968 B2 | 10/2014 | Giusti | |
| 8,905,965 B2 | 12/2014 | Mandro et al. | |
| 8,905,981 B2 | 12/2014 | Budig et al. | |
| 9,296,508 B2 | 3/2016 | Kanfer et al. | |
| 9,352,318 B2 | 5/2016 | Giusti | |
| 9,422,089 B2 | 8/2016 | Wheeler | |
| 9,610,220 B2 | 4/2017 | Andersson et al. | |
| 2003/0073974 A1 | 4/2003 | Falconer | |
| 2004/0097997 A1 | 5/2004 | Di Cecco | |
| 2005/0067031 A1 * | 3/2005 | Lee | F15B 13/0402 |
| | | | 137/625.69 |
| 2005/0070933 A1 | 3/2005 | Leiboff | |
| 2005/0148954 A1 | 7/2005 | Abell | |
| 2005/0277811 A1 | 12/2005 | Richards et al. | |
| 2006/0025728 A1 | 2/2006 | Leiboff et al. | |
| 2006/0025729 A1 | 2/2006 | Leiboff et al. | |
| 2006/0142737 A1 | 6/2006 | Tanghoj | |
| 2006/0150310 A1 | 7/2006 | Tsai | |
| 2006/0180585 A1 | 8/2006 | Cunningham et al. | |
| 2007/0073216 A1 | 3/2007 | McAuliffe et al. | |
| 2008/0065001 A1 | 3/2008 | DiNucci et al. | |
| 2009/0054876 A1 | 2/2009 | Borodulin | |
| 2009/0166361 A1 | 7/2009 | Lourenco | |
| 2010/0106236 A1 | 4/2010 | Nelson | |
| 2010/0191183 A1 | 7/2010 | Tanghoej et al. | |
| 2010/0211050 A1 | 8/2010 | Luther | |
| 2010/0249752 A1 | 9/2010 | Tanghoej | |
| 2010/0280490 A1 | 11/2010 | Schertiger | |
| 2010/0324540 A1 | 12/2010 | Paulen et al. | |
| 2011/0060317 A1 | 3/2011 | Frojd | |
| 2011/0144588 A1 | 6/2011 | Taylor et al. | |
| 2011/0224653 A1 | 9/2011 | Torstensen | |
| 2011/0295236 A1 | 12/2011 | Gregory | |
| 2012/0016318 A1 | 1/2012 | Hoang et al. | |
| 2012/0143168 A1 | 6/2012 | Bjerregaard | |
| 2012/0179144 A1 | 7/2012 | Carleo | |
| 2012/0271281 A1 | 10/2012 | Schertiger | |
| 2013/0068767 A1 | 3/2013 | Fraser et al. | |
| 2013/0099476 A1 | 4/2013 | Chevereau et al. | |
| 2013/0131626 A1 * | 5/2013 | Thompson | A61M 39/223 |
| | | | 604/500 |
| 2013/0134123 A1 | 5/2013 | Fraser | |
| 2013/0161344 A1 | 6/2013 | Park et al. | |
| 2013/0218136 A1 | 8/2013 | Tanghoej et al. | |
| 2013/0237920 A1 | 9/2013 | Kokenis | |
| 2013/0245380 A1 | 9/2013 | Vogel | |
| 2013/0289537 A1 | 10/2013 | Schertiger | |
| 2013/0292286 A1 | 11/2013 | Van Groningen | |
| 2013/0331781 A1 | 12/2013 | Andreen | |
| 2014/0005602 A1 | 1/2014 | Andreen et al. | |
| 2014/0155864 A1 | 6/2014 | Andreen | |
| 2014/0262860 A1 | 9/2014 | Hagel | |
| 2014/0263436 A1 | 9/2014 | Gelov et al. | |
| 2014/0276631 A1 | 9/2014 | Gilman | |
| 2014/0360896 A1 | 12/2014 | Torstensen | |
| 2015/0094660 A1 | 4/2015 | Mandro et al. | |
| 2015/0290372 A1 * | 10/2015 | Muller | A61M 60/816 |
| | | | 600/16 |
| 2016/0001033 A1 * | 1/2016 | Van De Ven | F16K 11/04 |
| | | | 137/625.48 |
| 2016/0016703 A1 | 1/2016 | Muhlemann | |
| 2016/0023818 A1 | 1/2016 | Gelov et al. | |
| 2016/0059999 A1 | 3/2016 | Fraser et al. | |
| 2016/0193403 A1 | 7/2016 | Andersson | |
| 2016/0228872 A1 | 8/2016 | Giusti | |
| 2017/0157314 A1 | 6/2017 | Andersson et al. | |

(56) References Cited

U.S. PATENT DOCUMENTS

| | | | |
|---|---|---|---|
| 2017/0252506 A1 | 9/2017 | Frostaa et al. | |
| 2017/0274135 A1 | 9/2017 | Frostaa et al. | |
| 2019/0224402 A1 | 7/2019 | Henry et al. | |

FOREIGN PATENT DOCUMENTS

| | | | |
|---|---|---|---|
| CN | 205307484 U | 6/2016 | |
| DE | 4114390 A1 | 11/1992 | |
| DE | 20117438 U1 | 3/2002 | |
| DE | 10213411 A1 | 10/2003 | |
| DE | 20317135 U1 | 2/2004 | |
| DE | 202005008071 U1 | 7/2005 | |
| DE | 202005009946 U1 | 9/2005 | |
| DE | 202006013663 U1 | 11/2006 | |
| DE | 202010006267 U1 | 11/2010 | |
| DE | 202010007433 U1 | 7/2011 | |
| DE | 102010060168 A1 | 4/2012 | |
| DE | 202011107025 | 3/2013 | |
| DE | 202011107059 | 3/2013 | |
| DE | 102013014483 A1 | 6/2014 | |
| EP | 0041487 A | 12/1981 | |
| EP | 0134630 A | 3/1985 | |
| EP | 0861639 A2 | 9/1998 | |
| EP | 0809520 B1 | 4/1999 | |
| EP | 0996542 A1 | 5/2000 | |
| EP | 1051984 A2 | 11/2000 | |
| EP | 1180373 A2 | 2/2002 | |
| EP | 1011754 B1 | 9/2004 | |
| EP | 1466645 A2 | 10/2004 | |
| EP | 1392575 B1 | 9/2005 | |
| EP | 1593710 A1 | 11/2005 | |
| EP | 1634554 A2 | 3/2006 | |
| EP | 1638856 A1 | 3/2006 | |
| EP | 1246655 B1 | 5/2006 | |
| EP | 1434611 B1 | 6/2006 | |
| EP | 1671663 A1 | 6/2006 | |
| EP | 1303243 B1 | 1/2007 | |
| EP | 1752175 A1 | 2/2007 | |
| EP | 1752176 A1 | 2/2007 | |
| EP | 1752177 A1 | 2/2007 | |
| EP | 1039858 B1 | 5/2007 | |
| EP | 1491223 B1 | 5/2007 | |
| EP | 1872814 A1 | 1/2008 | |
| EP | 1878461 A1 | 1/2008 | |
| EP | 1897579 A1 | 3/2008 | |
| EP | 1897580 A1 | 3/2008 | |
| EP | 1946785 A1 | 7/2008 | |
| EP | 1946786 A1 | 7/2008 | |
| EP | 1372755 B1 | 8/2008 | |
| EP | 0915715 B1 | 9/2008 | |
| EP | 1531885 B1 | 10/2008 | |
| EP | 1977778 A1 | 10/2008 | |
| EP | 1982741 A2 | 10/2008 | |
| EP | 1514572 B1 | 12/2008 | |
| EP | 2027832 A2 | 2/2009 | |
| EP | 2042211 A1 | 4/2009 | |
| EP | 2044963 A1 | 4/2009 | |
| EP | 2060296 A1 | 5/2009 | |
| EP | 2072075 A1 | 6/2009 | |
| EP | 2106821 A1 | 10/2009 | |
| EP | 2035292 B1 | 5/2010 | |
| EP | 2251454 A2 | 11/2010 | |
| EP | 2468326 A1 | 12/2010 | |
| EP | 2211937 B1 | 7/2011 | |
| EP | 2125070 B1 | 4/2012 | |
| EP | 2452706 A2 | 5/2012 | |
| EP | 2468319 A1 | 6/2012 | |
| EP | 2005981 B1 | 9/2012 | |
| EP | 1909864 B1 | 10/2012 | |
| EP | 2504054 A1 | 10/2012 | |
| EP | 2515985 A1 | 10/2012 | |
| EP | 2224976 B1 | 2/2013 | |
| EP | 2229196 B1 | 2/2013 | |
| EP | 2158926 B1 | 5/2013 | |
| EP | 2596831 A2 | 5/2013 | |
| EP | 2242696 B1 | 6/2013 | |
| EP | 2617316 A2 | 7/2013 | |
| EP | 2638927 A2 | 9/2013 | |
| EP | 2671601 A1 | 11/2013 | |
| EP | 2671602 A1 | 12/2013 | |
| EP | 2679259 A1 | 1/2014 | |
| EP | 2679260 A1 | 1/2014 | |
| EP | 2679261 A1 | 1/2014 | |
| EP | 2682069 A1 | 1/2014 | |
| EP | 2686054 A1 | 1/2014 | |
| EP | 2703019 A1 | 3/2014 | |
| EP | 2416819 B1 | 8/2014 | |
| EP | 1752174 B1 | 9/2014 | |
| EP | 2774648 A1 | 9/2014 | |
| EP | 2470237 B1 | 10/2014 | |
| EP | 2683424 B1 | 7/2015 | |
| EP | 1728527 B1 | 3/2016 | |
| EP | 2810669 B1 | 4/2016 | |
| EP | 2576374 B1 | 9/2016 | |
| FR | 2961886 B1 | 3/1987 | |
| FR | 2717676 A1 | 9/1995 | |
| GB | 2031735 A | 4/1980 | |
| GB | 2033231 A | 5/1980 | |
| GB | 2322079 A | 8/1998 | |
| GB | 2496900 A | 5/2013 | |
| JP | 2001025473 | 1/2001 | |
| KR | 20110101674 | 7/2012 | |
| WO | WO 1987001596 | 3/1987 | |
| WO | WO 96-08219 A1 | 3/1996 | |
| WO | WO 96-25188 A1 | 8/1996 | |
| WO | WO 96-31250 A1 | 10/1996 | |
| WO | WO 97-15335 A1 | 5/1997 | |
| WO | WO 97-26937 A1 | 7/1997 | |
| WO | WO 97-41811 A2 | 11/1997 | |
| WO | WO 97-49441 A1 | 12/1997 | |
| WO | WO 98-11932 A1 | 3/1998 | |
| WO | WO 98-19729 A1 | 5/1998 | |
| WO | WO 98-20722 A2 | 5/1998 | |
| WO | WO 98-23312 A1 | 6/1998 | |
| WO | WO 99-30652 A1 | 6/1999 | |
| WO | WO 99-30761 A1 | 6/1999 | |
| WO | WO 99-42155 A2 | 8/1999 | |
| WO | WO 99-59656 A1 | 11/1999 | |
| WO | WO 00-16843 A1 | 3/2000 | |
| WO | WO 00-30575 A1 | 6/2000 | |
| WO | WO 00-47494 A1 | 8/2000 | |
| WO | WO 01-43807 A1 | 6/2001 | |
| WO | WO 01-49345 A1 | 7/2001 | |
| WO | WO 01-60255 A1 | 8/2001 | |
| WO | WO 02-07668 A1 | 1/2002 | |
| WO | WO 02-13887 A1 | 2/2002 | |
| WO | WO 02-060361 A2 | 8/2002 | |
| WO | WO 02-074363 A2 | 9/2002 | |
| WO | WO 02-080843 A2 | 10/2002 | |
| WO | WO 03-001994 A1 | 1/2003 | |
| WO | WO 03-008028 A2 | 1/2003 | |
| WO | WO 03-008029 A2 | 1/2003 | |
| WO | WO 03-022561 A1 | 3/2003 | |
| WO | WO 03-030967 A1 | 4/2003 | |
| WO | WO 03-030968 A1 | 4/2003 | |
| WO | WO 03-030969 A1 | 4/2003 | |
| WO | WO 03-045487 A2 | 6/2003 | |
| WO | WO 03-061732 A2 | 7/2003 | |
| WO | WO 03-063668 A1 | 8/2003 | |
| WO | WO 03-092779 A1 | 11/2003 | |
| WO | WO 03-097237 A2 | 11/2003 | |
| WO | WO 2004/006993 A1 | 1/2004 | |
| WO | WO 2004/021890 A1 | 3/2004 | |
| WO | WO 2004/032750 A1 | 4/2004 | |
| WO | WO 2004/035123 A1 | 4/2004 | |
| WO | WO 2004/050155 A1 | 6/2004 | |
| WO | WO 2004/054446 A1 | 7/2004 | |
| WO | WO 2004/060259 A2 | 7/2004 | |
| WO | WO 2004/103153 A2 | 12/2004 | |
| WO | WO 2004/112712 A2 | 12/2004 | |
| WO | WO 2005/003725 A2 | 1/2005 | |
| WO | WO 2005/004964 A1 | 1/2005 | |
| WO | WO 2005/004970 A1 | 1/2005 | |
| WO | WO 2005/014055 A2 | 2/2005 | |

(56) References Cited

FOREIGN PATENT DOCUMENTS

| | | | |
|---|---|---|---|
| WO | WO 2005/032617 | A2 | 4/2005 |
| WO | WO 2006/005349 | A2 | 1/2006 |
| WO | WO 2006/010556 | A1 | 2/2006 |
| WO | WO 2006/015223 | A2 | 2/2006 |
| WO | WO 2006/017439 | A2 | 2/2006 |
| WO | WO 2006/024205 | A1 | 3/2006 |
| WO | WO 2006/044249 | A2 | 4/2006 |
| WO | WO 2006/044621 | A2 | 4/2006 |
| WO | WO 2006/045809 | A1 | 5/2006 |
| WO | WO 2006/121183 | A1 | 11/2006 |
| WO | WO 2006/135934 | A2 | 12/2006 |
| WO | WO 2007/005851 | A2 | 1/2007 |
| WO | WO 2007/022223 | A2 | 2/2007 |
| WO | WO 2007/038988 | A1 | 4/2007 |
| WO | WO 2007/050685 | A2 | 5/2007 |
| WO | WO 2007/081264 | A1 | 7/2007 |
| WO | WO 2007/082540 | A1 | 7/2007 |
| WO | WO 2007-103995 | A2 | 9/2007 |
| WO | WO 2007/106356 | A2 | 9/2007 |
| WO | WO 2007/106431 | A2 | 9/2007 |
| WO | WO 2007/111891 | A2 | 10/2007 |
| WO | WO 2007/121137 | A2 | 10/2007 |
| WO | WO 2008/024136 | A1 | 2/2008 |
| WO | WO 2008/030999 | | 3/2008 |
| WO | WO 2008/039910 | A2 | 4/2008 |
| WO | WO 2008-048856 | A2 | 4/2008 |
| WO | WO 2008-058160 | A2 | 5/2008 |
| WO | WO 2008-087220 | A1 | 7/2008 |
| WO | WO 2008-087221 | A2 | 7/2008 |
| WO | WO 2008/089081 | A1 | 7/2008 |
| WO | WO 2008/090551 | A2 | 7/2008 |
| WO | WO 2008/137353 | A1 | 11/2008 |
| WO | WO 2009/010070 | A1 | 1/2009 |
| WO | WO 2009/010975 | A1 | 1/2009 |
| WO | WO 2009-015152 | A1 | 1/2009 |
| WO | WO 2009/017541 | A1 | 2/2009 |
| WO | WO 2009-056906 | A1 | 5/2009 |
| WO | WO 2009/066163 | A1 | 5/2009 |
| WO | WO 2009/080050 | A1 | 7/2009 |
| WO | WO 2009/080051 | A1 | 7/2009 |
| WO | WO 2011/023196 | A1 | 8/2009 |
| WO | WO 2009-128109 | A1 | 10/2009 |
| WO | WO 2009/139878 | A1 | 11/2009 |
| WO | WO 2009-144028 | A1 | 12/2009 |
| WO | WO 2009-153973 | A1 | 12/2009 |
| WO | WO 2010/006620 | A1 | 1/2010 |
| WO | WO 2010/047501 | A2 | 4/2010 |
| WO | WO 2010/057208 | A1 | 5/2010 |
| WO | WO 2010/077980 | A1 | 7/2010 |
| WO | WO 2010/115430 | A1 | 10/2010 |
| WO | WO 2010/115431 | A2 | 10/2010 |
| WO | WO 2010/126586 | A1 | 11/2010 |
| WO | WO 2010/130261 | A1 | 11/2010 |
| WO | WO 2011/011023 | | 1/2011 |
| WO | WO 2011/012323 | A1 | 2/2011 |
| WO | WO 2011/018092 | A1 | 2/2011 |
| WO | WO 2011/019359 | A1 | 2/2011 |
| WO | WO 2011/026929 | A1 | 3/2011 |
| WO | WO 2011/034911 | A1 | 3/2011 |
| WO | WO 2011-075581 | A1 | 6/2011 |
| WO | WO 2011/079129 | A1 | 6/2011 |
| WO | WO 2011/105644 | A1 | 9/2011 |
| WO | WO 2011/109393 | A1 | 9/2011 |
| WO | WO 2011/139498 | A1 | 11/2011 |
| WO | WO 2011/147803 | A1 | 12/2011 |
| WO | WO 2011/160834 | A1 | 12/2011 |
| WO | WO 2012/006629 | A2 | 1/2012 |
| WO | WO 2012/013662 | A1 | 2/2012 |
| WO | WO 2012/016179 | A1 | 2/2012 |
| WO | WO 2012/016570 | A2 | 2/2012 |
| WO | WO 2012/016571 | A2 | 2/2012 |
| WO | WO 2012/079590 | A1 | 6/2012 |
| WO | WO 2012/085107 | A2 | 6/2012 |
| WO | WO 2012/110755 | A2 | 8/2012 |
| WO | WO 2012/120456 | A2 | 9/2012 |
| WO | WO 2012/134804 | A1 | 10/2012 |
| WO | WO 2012/154946 | A1 | 11/2012 |
| WO | WO 2012/156478 | A1 | 11/2012 |
| WO | WO 2012/164559 | A1 | 12/2012 |
| WO | WO 2012/166045 | A1 | 12/2012 |
| WO | WO 2012/166967 | A1 | 12/2012 |
| WO | WO 2013/026564 | A1 | 2/2013 |
| WO | WO 2013/026565 | A1 | 2/2013 |
| WO | WO 2013/029620 | A1 | 3/2013 |
| WO | WO 2013/029621 | A1 | 3/2013 |
| WO | WO 2013/029622 | A1 | 3/2013 |
| WO | WO 2013/075725 | A1 | 5/2013 |
| WO | WO 2013/076446 | A1 | 5/2013 |
| WO | WO 2013/083137 | A1 | 6/2013 |
| WO | WO 2013/090778 | A1 | 6/2013 |
| WO | WO 2013/098190 | A1 | 7/2013 |
| WO | WO 2013/105091 | A1 | 7/2013 |
| WO | WO 2013/163364 | A1 | 10/2013 |
| WO | WO 2013/182593 | A1 | 12/2013 |
| WO | WO 2013/184158 | A1 | 12/2013 |
| WO | WO 2014/001292 | A1 | 1/2014 |
| WO | WO 2014/001313 | A1 | 1/2014 |
| WO | WO 2014/001322 | A1 | 1/2014 |
| WO | WO 2014/062225 | A1 | 4/2014 |
| WO | WO 2014/063711 | A1 | 5/2014 |
| WO | WO 2014-064414 | A1 | 5/2014 |
| WO | WO 2014/074142 | A1 | 5/2014 |
| WO | WO 2014/074147 | A1 | 5/2014 |
| WO | WO 2014/081859 | A1 | 5/2014 |
| WO | WO 2014/085597 | A1 | 6/2014 |
| WO | WO 2014-089278 | A1 | 6/2014 |
| WO | WO 2014/093056 | A1 | 6/2014 |
| WO | WO 2014/139767 | | 9/2014 |
| WO | WO 2014/140328 | A1 | 9/2014 |
| WO | WO 2014/142895 | A1 | 9/2014 |
| WO | WO 2014/142917 | A1 | 9/2014 |
| WO | WO 2014/142923 | A1 | 9/2014 |
| WO | WO 2014/142930 | A1 | 9/2014 |
| WO | WO 2014/144714 | | 9/2014 |
| WO | WO 2014/145211 | A2 | 9/2014 |
| WO | WO 2014/147620 | A1 | 9/2014 |
| WO | WO 2014/149276 | A1 | 9/2014 |
| WO | WO 2014/159869 | A2 | 10/2014 |
| WO | WO 2014/165046 | A1 | 10/2014 |
| WO | WO 2014/176486 | A1 | 10/2014 |
| WO | WO 2014/176867 | A1 | 11/2014 |
| WO | WO 2015/031851 | | 3/2015 |
| WO | WO 2015/117141 | | 8/2015 |
| WO | WO 2015/184365 | | 12/2015 |
| WO | WO 2016/095928 | A1 | 6/2016 |
| WO | WO 2016/095929 | A1 | 6/2016 |
| WO | WO 2016/095930 | A1 | 6/2016 |
| WO | WO 2017/101954 | A1 | 6/2017 |
| WO | 20180183128 | A1 | 10/2018 |

OTHER PUBLICATIONS

International Search Report dated Feb. 24, 2015, for International Application No. PCT/US2014/053573.

International Search Report and Written Opinion Dated Oct. 30, 2020 for International Application No. PCT/ US2020/039577.

* cited by examiner

SPOOL VALVE FOR BODY CAVITY IRRIGATION DEVICES

CROSS-REFERENCE TO RELATED APPLICATION

This application is a National Stage Entry of International Application No. PCT/US2020/039577 filed Jun. 25, 2020, which claims the benefit of U.S. Provisional Patent Application Ser. No. 62/882,246, filed Aug. 2, 2019, all of which are hereby incorporated by reference in their entirety.

FIELD OF THE DISCLOSURE

The present disclosure is directed to flow control within body cavity irrigation devices, and more particularly to a spool valve and a method of using the spool valve in body cavity irrigation devices.

More particularly, the disclosure provides a spool valve for use in cavity irrigation devices such as for use in an electromechanical rectal irrigation (RI) or stoma irrigation (SI) device, which may alternatively be referred to as a trans-anal irrigation (TAI) device, wherein the device has a base unit and a controller, such as is disclosed in International Patent Application No. PCT/US17/41205, which is incorporated herein by reference in its entirety.

BACKGROUND

Many individuals suffering spinal cord injury (SCI) and other medical conditions (e.g., cauda equina syndrome, multiple sclerosis (MS), spina bifida (SB), and chronic constipation) may need to avail themselves of bowel management treatments, in many cases along with a bladder management program. For SCI users, the issues of independence, dexterity, and ease of use are important needs that must be addressed by a bowel management program. Users can avail themselves of various solutions such as pharmacological (laxatives/suppository), digital stimulation, diet control and others, with the aim of having a regular bowel management routine without constipation or fecal incontinence.

TAI provides another option for bowel management. RI is the delivery of irrigating liquid into the colon to flush the body's system of stool and create pseudo-continence for the end user. Devices currently on the market allow the user to utilize a product over the toilet, in a commode/shower chair or in a bed to introduce water into the bowel through a rectal catheter. The user will introduce an amount of water into the bowel (typically 500-700 mL) in order to flush out stool located in the bowel passage. It is common for the user to introduce the water, wait for a period of time and allow gravity to flush the water and stool out of the body. The rectal catheter may have an inflatable/deflatable balloon to assist in retention of the catheter during water introduction. The balloon is typically inflated by a fluid such as air or water. Thus, there may be various tubing sets specifically configured for each type of use.

The typical RI device has an irrigation liquid reservoir and a pump base unit which contains a pump for pumping water from the reservoir through suitable tubing to the catheter. RI devices may use water to inflate a balloon of a rectal catheter. The devices may have a single-lumen tubing from a reservoir into a controller, and dual-lumen tubing from the controller to the catheter. One of the dual lumens may enable the rectal catheter balloon to be inflated with water and later deflated; while the second lumen may accommodates water transfer from the reservoir into the rectum. The device may provide that when the catheter balloon is deflated, a liquid communication channel is created so that water returning from the deflated balloon travels via the controller into the lumen toward the catheter, i.e. the water from the deflated balloon does not return to the water reservoir.

Thus, fluid tubing sets may contain two separate lumens, one for irrigation fluid or irrigant, and one for retention balloon inflation/deflation. With such a device, it is desirable that neither of the tubing lumens ever communicates with the other lumen during a RI procedure, so there is no fluid communication between the lumens. This may be accomplished, for example, as shown in the above-identified International Patent Application No. PCT/US17/41205, via use of a fluid control or hydraulic control circuit having a pump and at least three solenoid valves within a base. The solenoid valves are used to regulate the flow of water within the hydraulic control circuit and to ensure that the water in the separate tubing lumens remains independent.

Hence, by design, all tubing lumens are independent of each other, and there is no condition of the hydraulic control circuit that permits the lumens to communicate with one other. This ensures that water from the deflated catheter balloon only returns to the water reservoir, and not into the catheter or the lumens in communication with the catheter. Alternatively, the fluid tubing set may contain three separate lumens, one for irrigant, one for waste control valve actuation, and one for retention balloon inflation/deflation. Accordingly, devices may be configured for use with different catheters, whether having a dual of triple lumen catheter.

Devices also may be configured for use with catheters that are intended for different treatment modalities. For instance, when a balloon catheter is being used with a pump base unit and controller, the device needs to be primed, the retention balloon is inflated, the irrigant is instilled, and the retention balloon is deflated. By comparison, when a cone catheter is being used with a base unit and controller, the device needs to be primed and then the irrigant is instilled. Accordingly, there may be modalities that involve use of a cone catheter, or a balloon catheter, where the balloon catheter may be usable, for example, in a procedure conducted over a toilet or in a bed. The variety of tubing sets and modalities can present challenges for users.

The device disclosed in the above-identified International Patent Application No. PCT/US17/41205 includes example embodiments having a pump base unit and a controller, along with a plurality of solenoid valves to regulate the flow of water within the hydraulic control circuit. The first example embodiment in International Patent Application No. PCT/US17/41205 uses three separate solenoid valves to control fluid flow, to perform three stages in an RI procedure. The three solenoid valves include a reservoir flow director valve, a pump flow director valve, and a tubing flow director valve. However, use of at least three solenoid valves may have certain disadvantages. The solenoid valves may be constructed using metal material for the components. For example, 316L stainless steel may be used to resist corrosion due to saline solution that may flow through the solenoid valves during testing, and water that may flow through the solenoid valves during use. Moreover, a device requiring three such stainless steel solenoid valves requires sufficient space to house the valves and adds expense and mass to the base unit.

SUMMARY

The present disclosure is directed to a body cavity irrigation device that includes a spool valve for use in controlling fluid flow within the irrigation device. The spool valve is used to regulate the flow of fluid depending on the stage of an irrigation procedure. The irrigation device may be used for RI or SI, generally referred to herein as TAI. The spool valve includes a valve body having an elongated bore and a plurality of ports that are spaced apart and in fluid communication with the bore. The ports also are in fluid communication with different components of the irrigation device. The spool valve also includes a spool that slides within the bore of the valve body. The spool includes a plurality of lands with seals, and a plurality of grooves, which are used to open and close the various ports of the spool valve in predetermined combinations that correspond to the position of the spool within the valve body and the desired stage of a procedure. In this manner, the spool valve is used within a hydraulic control circuit to control fluid flow within the passages of the device. The spool may be moved by an actuator, such as a linear actuator, motor or other device directly or through a drive mechanism that provides translational movement to the spool. The actuator is used to move the spool to different positions within the valve body to control fluid flow during the various stages of operation of a TAI procedure.

The spool valve may replace multiple solenoid valves, providing numerous advantages. For example, with respect to the first embodiment of the aforementioned International Patent Application No. PCT/US17/41205, incorporated by reference in its entirety herein, the spool valve advantageously requires a smaller footprint for the hydraulic control circuit within the pump base unit. Also, a single actuator may be used to move the spool, replacing for example three solenoids that otherwise may be used for actuation of three solenoid valves that would be needed to provide a similar hydraulic control circuit.

Additionally, the spool valve components may be molded or otherwise constructed of less expensive and lighter weight materials that do not corrode. For instance, polymer materials may be used to construct the spool and valve body and polymer or rubber materials may be used to construct the seals disposed between the spool and bore of the valve body. The corrosion resistant, lighter weight spool valve having a more compact arrangement advantageously may be used within a device that includes a pump base unit, an irrigation fluid reservoir, an electronic controller, and may be in fluid communication with conduits used in RI, SI, TAI or other irrigation devices, while providing an opportunity to use a single actuator to move the spool so as to control the fluid flow during the stages of a procedure. Such a device provides technical solutions to multiple technical problems by providing a device with a single actuator and that is more compact, lighter weight and more corrosion resistant.

It will be appreciated that the spool valve may be used with the controller to adjust the intended modality and to provide the proper operative procedures associated with a respective tubing set. The usability of a balloon catheter, for instance, to perform an RI procedure may involve the following steps: (1) prime the device (without the catheter attached); (2) attach the catheter and insert it safely inside the rectum; (3) inflate the retention balloon; (4) instill irrigation; (5) deflate the retention balloon; and (6) remove the catheter. The first two steps are conducted in preparation for the three stages set forth in steps 3-5. Those three stages are followed by removal of the catheter. The spool valve provides inlet/outlet ports for separate flow paths for communication with the tubing set. The spool valve effectively replaces the three solenoid valves discussed in the first example embodiment in PCT/US17/41205 and provides fluid control within the hydraulic control circuit useful in performing steps 3-5 of the aforementioned procedure.

In one aspect, the present disclosure provides a trans-anal irrigation device having a spool valve, the device including a pump, an irrigation fluid reservoir in fluid communication with the pump, a rectal catheter having a retention balloon and an irrigant passage through the rectal catheter, fluid tubing having at least two lumens, a first lumen providing fluid communication between the pump and the retention balloon, and a second lumen providing fluid communication between the pump and the irrigant passage. The device also includes a hydraulic control circuit including a spool valve having a spool that is movable by an actuator. The spool valve includes a valve body having an elongated bore and a plurality of ports spaced apart along and in fluid communication with the elongated bore. The spool further includes a plurality of lands separated by a plurality of grooves, and seals extending outward from the lands and sealingly engaging the elongated bore of the valve body. The plurality of ports and plurality of seals and grooves are arranged for selectively directing flow alternatively from the reservoir to the retention balloon, from the reservoir to the irrigant passage, or from the retention balloon to the reservoir, based on the position of the spool within the valve body.

In an additional aspect, the present disclosure provides a spool valve for use in a hydraulic control circuit of a trans-anal irrigation device, including a spool valve having a valve body including an elongated bore and a spool that is movable within the bore, an actuator that moves the spool relative to the bore, the spool valve further including a plurality of ports spaced apart along and in fluid communication with the bore. The spool further includes a plurality of lands and a plurality of seals extending radially outward from the lands and sealingly engaging the spool and the bore of the valve body, and the plurality of ports and plurality of seals and grooves are arranged for selectively directing flow through at least two passages in at least three alternative configurations based on the position of the spool within the bore of the spool valve.

In a further aspect, the present disclosure provides a method of establishing fluid paths through a spool valve in a hydraulic control circuit of a trans-anal irrigation device, wherein the spool valve includes a valve body having an elongated bore and a plurality of ports spaced apart along and in fluid communication with the bore, and a spool that is movable within the bore, and wherein the plurality of ports further includes a first port associated with a pump outlet, a second port associated with a reservoir, a third port associated with a pump inlet, a fourth port associated with a pump inlet, a fifth port associated with a retention balloon lumen, a sixth port associated with a pump outlet, and a seventh port associated with an irrigant lumen. The method includes the steps of moving the spool to a first position within the bore of the valve body wherein the second port is in fluid communication with the third port and the fifth port is in fluid communication with the sixth port, so as to establish fluid paths through the spool valve from the reservoir to the pump inlet and from the pump outlet to the retention balloon lumen; moving the spool to a second position within the bore of the valve body wherein the second port is in fluid communication with the third and fourth ports and the sixth port is in fluid communication with the seventh port, so as to establish fluid paths through the spool valve from the reservoir to the pump inlet and from the pump outlet to the irrigant lumen; and moving the spool to a third position within the bore of the valve body wherein the first port is in fluid communication with the second portion and the fourth port is in fluid communication with the fifth port, so as to establish fluid paths through the spool valve from the retention balloon lumen to the pump inlet and from the pump outlet to the reservoir.

BRIEF DESCRIPTION OF THE DRAWINGS

In describing the preferred embodiments, reference is made to the accompanying drawing figures wherein like parts have like reference numerals, and wherein.

It should be understood that the drawings are not to scale. While some mechanical details of the example spool valve for use in cavity irrigation devices, including other plan and section views of the particular components, have not been shown, such details are considered to be within the comprehension of those skilled in the art in light of the present disclosure. It also should be understood that the present disclosure and claims are not limited to the preferred embodiments illustrated.

DETAILED DESCRIPTION OF THE EMBODIMENTS

Figure 1:
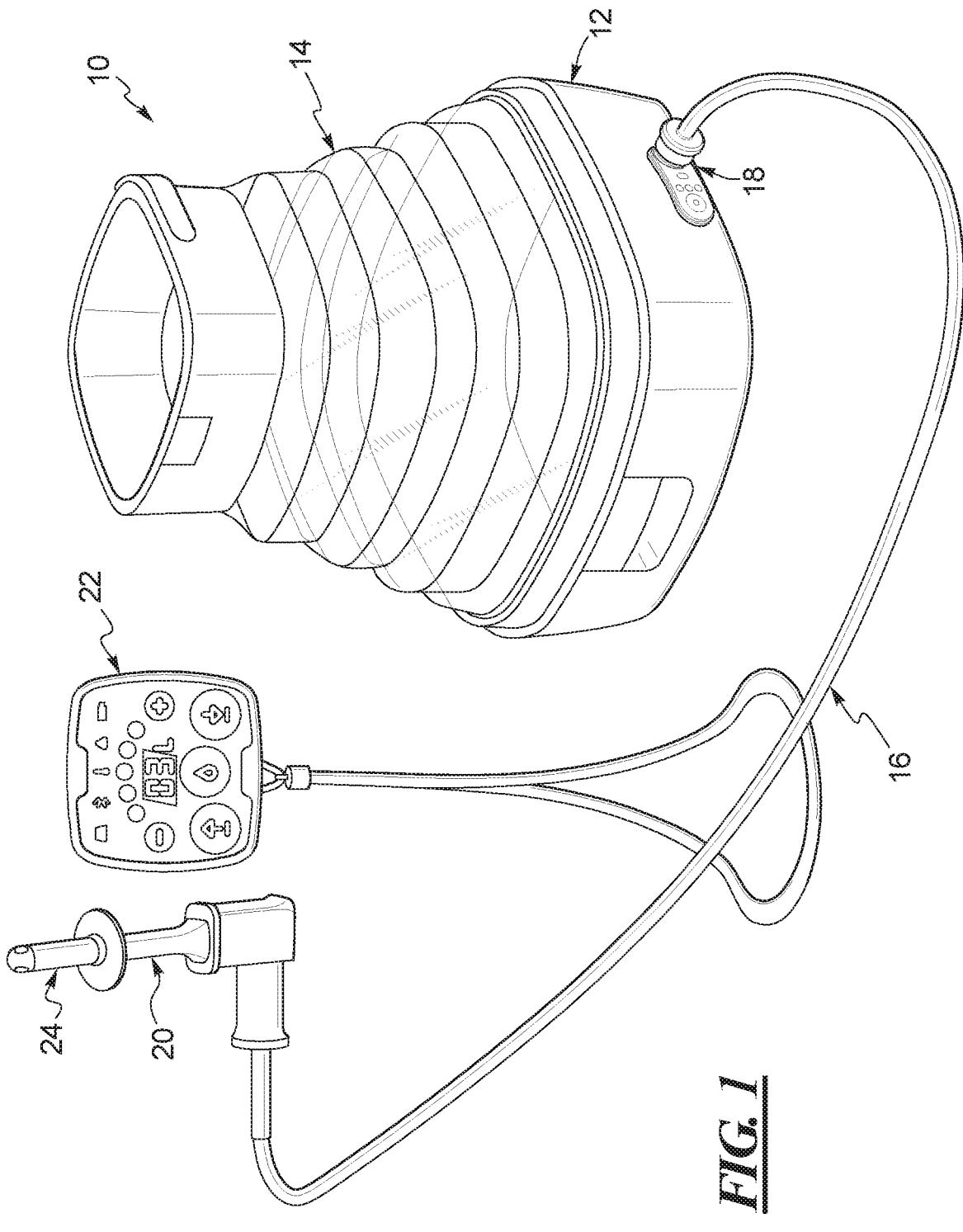
FIG. 1 is a simplified perspective view of an example body cavity irrigation device having a pump base unit, an irrigation fluid reservoir, an electronic controller, shown as optionally wireless, and a fluid tubing set.

The present disclosure relates to components for use in an electromechanical body irrigation device 10, such as a rectal irrigation (RI), stoma irrigation (SI) or trans-anal irrigation (TAI) device. A simplified view of such a system 10 is shown in FIG. 1. The system 10 may include a pump base unit 12, an irrigation fluid reservoir 14, a fluid tubing 16, a tubing connector 18, a disposable rectal catheter 20 and a wireless controller 22. The controller 22 is shown in this example in the form of a separate controller that may communicate wirelessly with the pump base unit 12. Alternatively, a controller for the system may be directly connected to or tethered by wired connection to the pump base unit 12. Also, the fluid reservoir 14 may be removable from the pump base unit 12, which in this example includes a connector 18 for establishing fluid communication with the proximal end of the fluid tubing 16.

As shown in FIG. 1, the fluid tubing 16 is connected at its distal end to the catheter 20. The catheter 20 has a retention balloon 24 that assists in sealingly holding the catheter 20 in the rectum. It will be appreciated that the retention balloon 24 may, for example, be attached to the exterior of the rectal catheter 20. The fluid tubing 16 of this example may include a retention balloon tube or lumen and an irrigant tube or lumen, such as disclosed in more detail in the first example embodiment in International Patent Application No. PCT/US17/41205, which is incorporated herein by reference.

Figure 2:
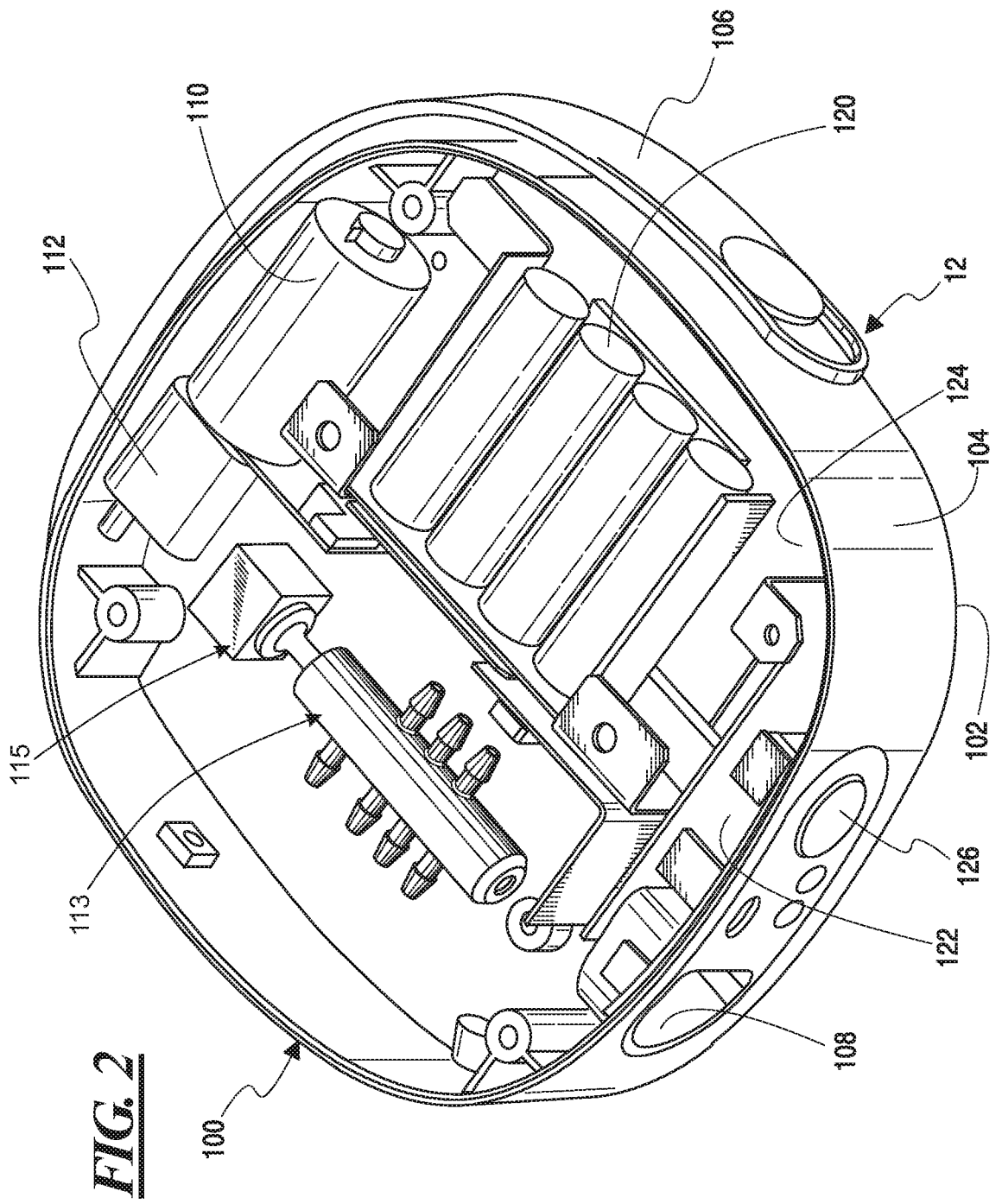
FIG. 2 is a perspective diagrammatic view of the pump base unit with the cover and reservoir removed to expose the pump, motor, spool valve, batteries and electronic control circuit boards.
Figure 3:
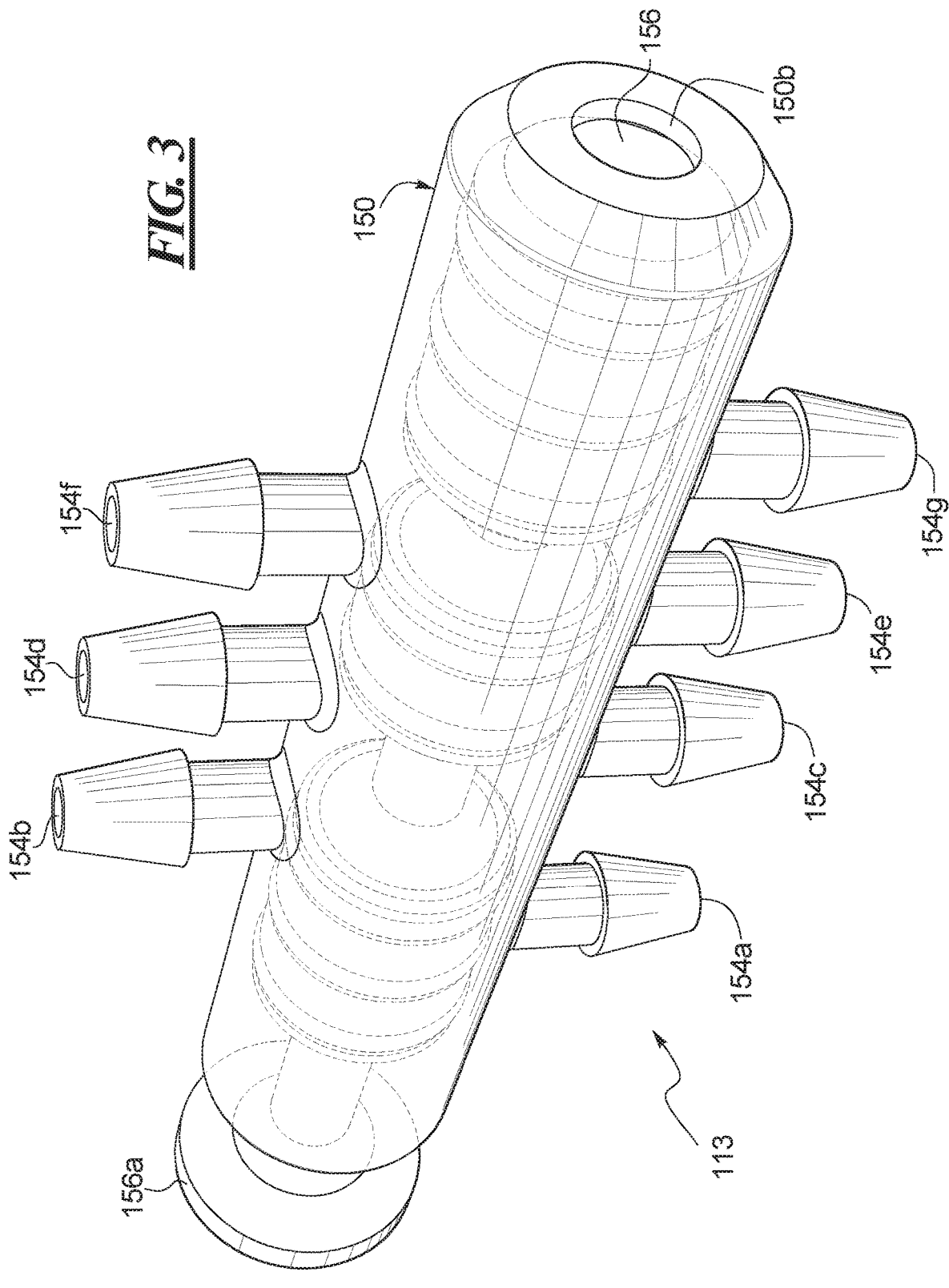
FIG. 3 is a perspective view of a spool valve of FIG. 2, showing a spool within a valve body, in a Stage 2 position to provide irrigant.
Figure 4:
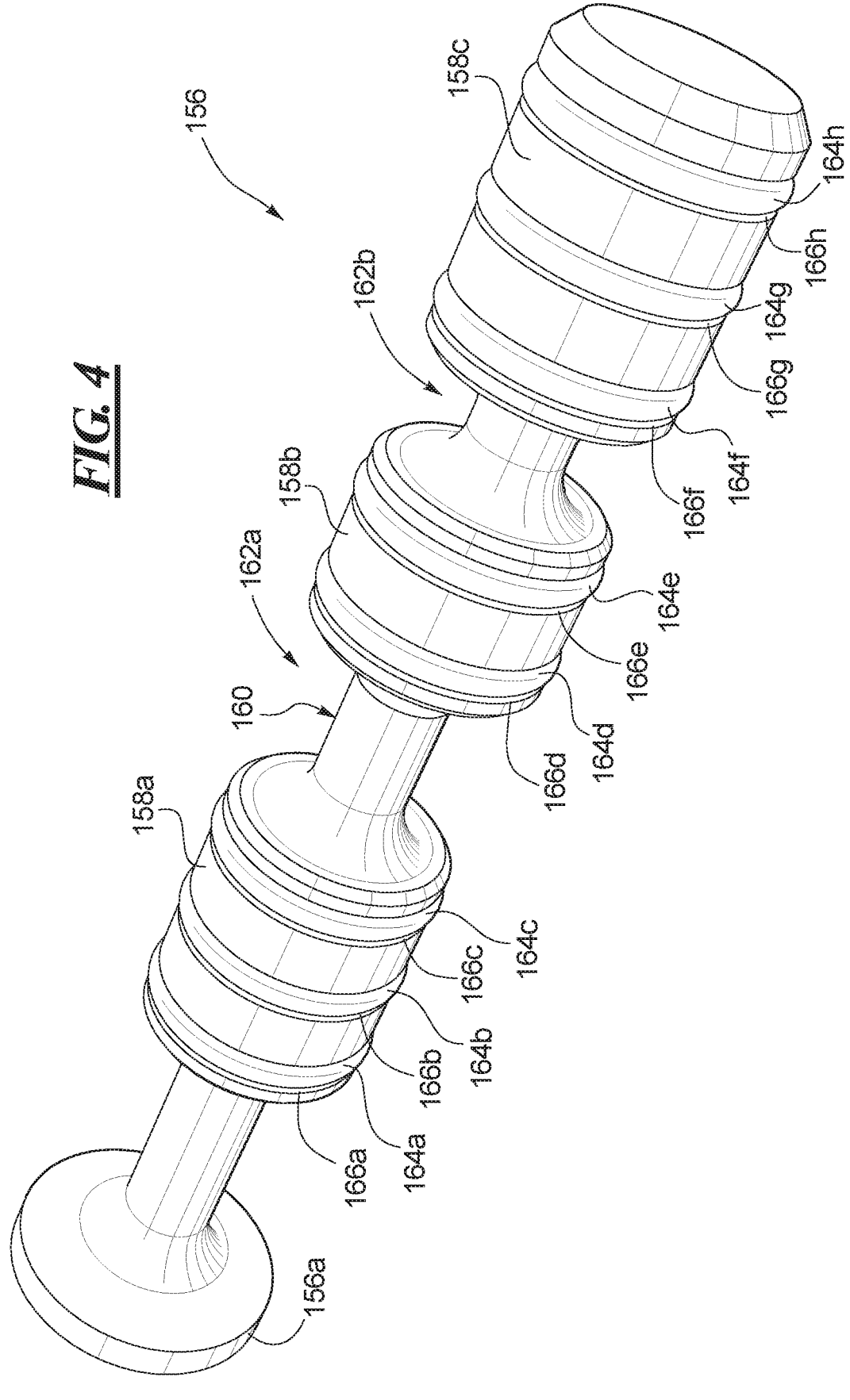
FIG. 4 is a perspective view of the spool of FIG. 3, showing the radially extending lands with seals.

Turning now to the pump base unit 12, FIG. 2 illustrates a generally hollow shell 100 which includes a floor 102 and a perimeter wall 104. The wall 104 is configured to support the base of the reservoir 14 when the reservoir is installed on the pump base unit 12. The wall 104 may have a handle 106 pivotably or otherwise connected to it. A user can grasp the handle 106 to carry the pump base unit 12. The wall 104 also has an opening 108 through it for mounting a fitting on the end of the tubing 16. The fitting allows connection of the tubing 16 and provides fluid communication between the pump and the fluid tubing 16 having a retention balloon lumen and an irrigant lumen.

Inside the shell 100 there is an electric motor 110, a pump 112, one example of which may be a one-way pump, and a spool valve 113 that is movably connected to an actuator 115. It will be appreciated that the pump 112 includes at least one pump inlet and at least one pump outlet. The spool valve 113 effectively replaces the hydraulic control circuit that was provided by the three solenoid valves of first example embodiment in International Patent Application No. PCT/US17/41205, allowing the pump base unit 12 of the present disclosure to otherwise operate similarly. The three solenoid valves being replaced include a reservoir flow director valve, a pump flow director valve, and a tubing flow director valve. The solenoid valves were normally-open, three-way valves.

Also present within the shell 100 is a rechargeable battery pack 120 for powering the pump 112, and internal tubing (not shown FIG. 2 for ease of viewing the other components), which provides various fluid connections and paths between the spool valve 113, the fluid reservoir 14, the pump 112 and the tubing 16. The fluid connections provided when using the spool valve 113 are in lieu of the connections of the internal tubing that are described in the fluid circuit diagrams shown for the first embodiment in International Patent Application No. PCT/US17/41205. Additionally located within the shell 100 are a power circuit board 122 and a controller printed circuit board 124. A power button 126 may be located on the outside of the shell 100 to turn on and off the pump base unit 12.

As shown in FIGS. 2-8, the spool valve 113 of the present example effectively replaces the aforementioned three solenoid valves in the device disclosed in FIGS. 1-14 of first example embodiment in International Patent Application No. PCT/US17/41205. It also will be appreciated that with respect to the additional embodiments in the aforementioned application that is incorporated by reference herein, use of the spool valve 113 could be accomplished to replace solenoid valves, so as to provide similar significant advantages. Accordingly, the spool valve 113 may provide a more compact, non-metallic, lighter weight, lower cost alternative to the use of at least three heavier and more expensive solenoid valves that may, for example, be constructed with stainless steel.

The spool valve 113 includes a valve body 150 having an elongated bore 152 is in fluid communication with a plurality ports 154a-154g that extend outward from the bore 152 and are spaced apart along the length of the bore 152. The plurality of ports 154a-154g include a first port 154a associated with an outlet of the pump 112, a second port 154b associated with the reservoir 14, a third port 154c associated with an inlet of the pump 112, a fourth port 154*d* associated with an inlet of the pump 112, a fifth port 154*e* associated with a retention balloon lumen of the tubing 16, a sixth port 154*f* associated with an outlet of the pump 112, and a seventh port 154*g* associated with an irrigant lumen of the tubing 16. The respective ports 154*a*-154*g* may be placed in fluid communication with different components of the irrigation device, as will be further described herein.

The spool valve 113 also includes a spool 156 that is slidably received by the bore 152 of the valve body 150. The valve body 150 has a proximal end opening 150*a* to the full diameter of the bore 152, which conveniently permits insertion of the spool 156 into the bore 152. The valve body 150 also has a distal end opening 150*b* having a smaller diameter, which provides an integrated stop for movement of the spool 156 in the distal direction, while also avoiding increased pressure or vacuum within the valve body 150 when moving the spool 156, which might otherwise restrict movement of the spool 156.

The spool 156 includes a base 156*a* at its proximal end, which provides for mounting to an actuator 115. The spool 156 also includes a plurality of lands, shown in this example as lands 158*a*-158*c*. Each land extends radially outward from a central stem 160 of the spool, and the lands 158*a*-158*c* are separated along the length of the stem 160 by a plurality of grooves 162*a*, 162*b*. The lands 158*a*-158*c* include a plurality of circumferential seals 164*a*-164*h*, such as O-ring seals, which in this example are received by circumferential channels 166*a*-166*h* in the respective lands 158*a*-158*c*.

The actuator 115, which may for example be a linear actuator, a motor with a linkage or other suitable alternative configuration, so as to provide translational or sliding movement to the spool 156 relative to the bore 152 of the valve body 150. The actuator 115 is controlled by the controller 22. The controller 22 causes the actuator 115 to slidably move the spool 156 relative to the bore 152 of the valve body 150. The multiple lands 158*a*-158*c* and seals 164*a*-164*h* extending over a significant length of the spool 156 provides for smooth sliding movement in the bore 152.

Movement of the spool 156 fore or aft along the bore 152 establishes different flow paths through the valve body 150. The seals 164*a*-164*h* and grooves 166*a*-166*h* effectively function to provide a hydraulic control circuit that opens and closes fluid pathways between ports 154*a*-154*g* of the valve body 150. Thus, the spool valve 113 is used to movably arrange fluid pathways that control fluid flow in the body cavity irrigation device 10. The spool 156 may be moved by the actuator 115 to different positions within the valve body 150 during operation of a TAI procedure.

Figure 6:
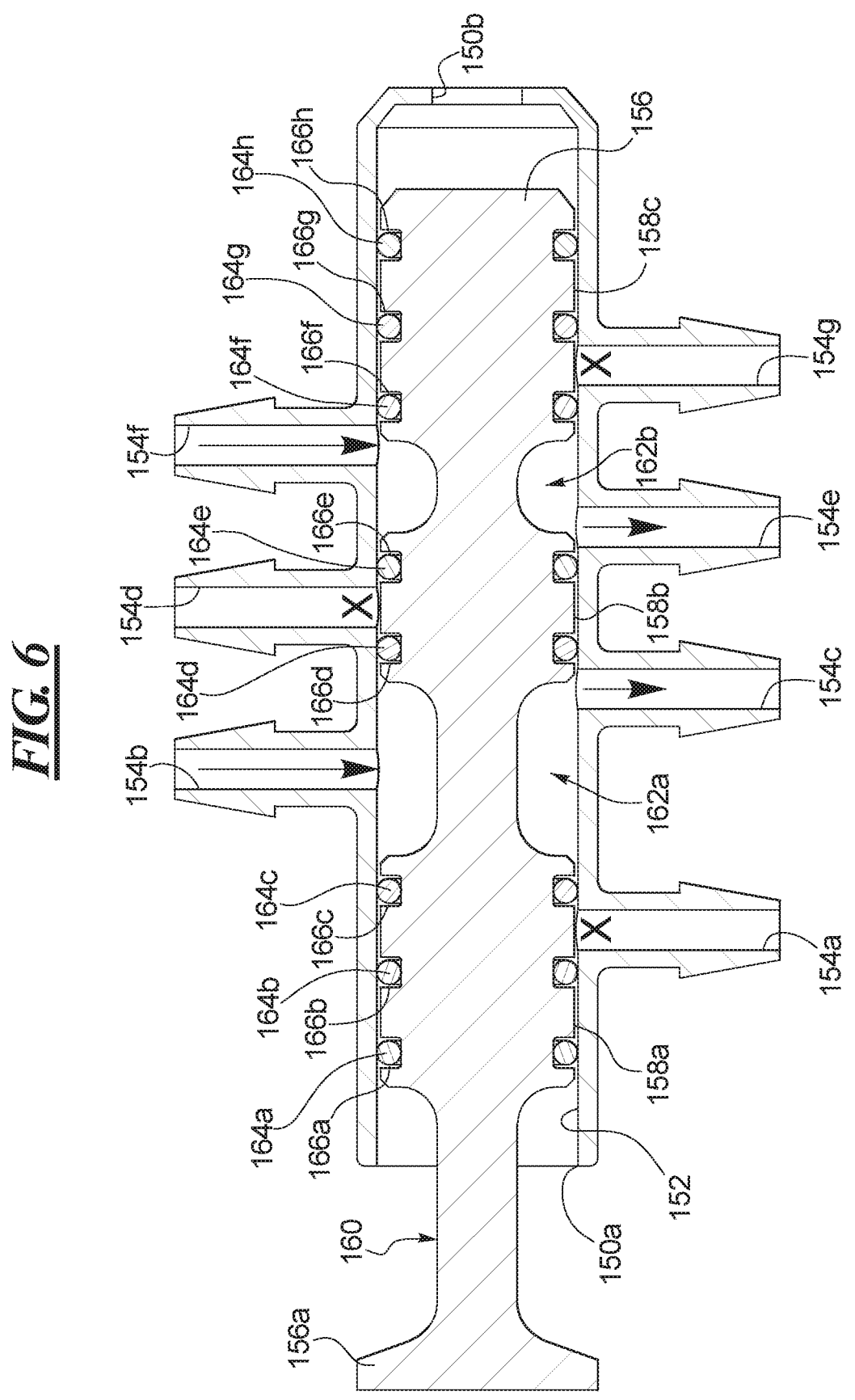
FIG. 6 is a cross-sectional side view of the spool valve of FIG. 2, showing the spool in a Stage 1 position to provide retention balloon inflation.

The specific placement of the seals 164*a*-164*h* and grooves 162*a*, 162*b* permit the single spool valve 113 to act as if it were three separate valves. For example, as shown in FIG. 6, the spool valve 113 is in a position that corresponds to Stage 1 of a procedure. In this position, three ports are effectively closed by being located between seals, namely, port 154*a* which is associated with the outlet of the pump 112 is closed by being located between seals 164*b* and 164*c*, while port 154*d* which is associated with the inlet of the pump 112 is closed by being located between seals 164*d* and 164*e*, and port 154*g* which is associated with the irrigant lumen is closed by being located between seals 164*f* and 164*g*. In this first position of the spool 156, two separate flow paths are provided, namely, port 154*b* which is associated with the reservoir 14 and port 154*c* which is associated with the inlet of the pump 112 are in fluid communication via groove 162*a* due to the location of seals 164*c* and

164*d*, while port 154*e* which is associated with the retention balloon lumen and port 154*f* which is associated with the outlet of the pump 112 are in fluid communication via groove 162*b* due to the location of seals 164*e* and 164*f*. Thus, this configuration permits fluid to be pumped from the reservoir to the retention balloon lumen, so as to inflate the retention balloon 24.

Figure 7:
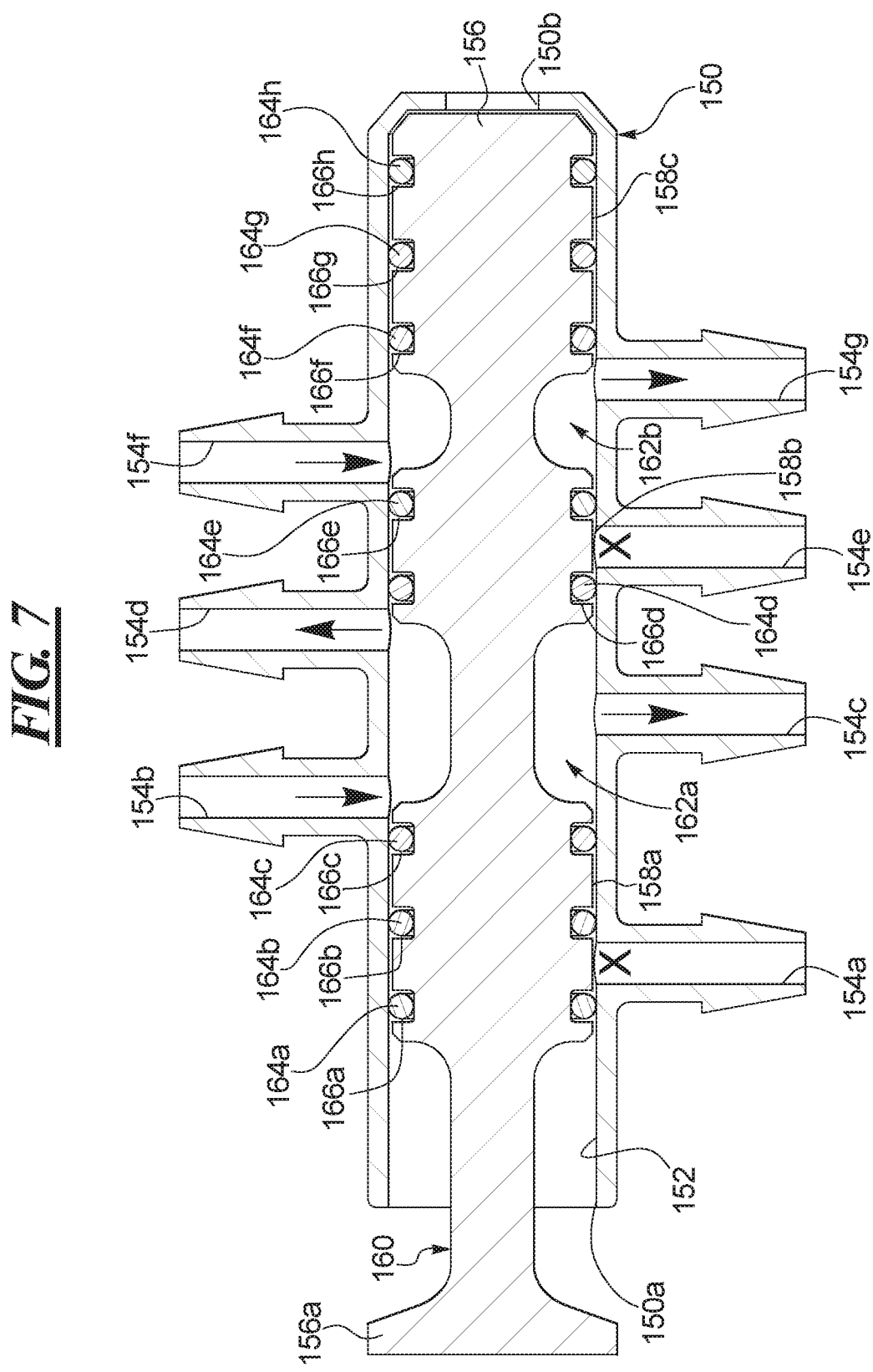
FIG. 7 is a cross-sectional side view of the spool valve of FIG. 2, showing the spool in a Stage 2 position to provide irrigant.

Referring to FIG. 7, the spool valve 113 has been moved and now is in a position that corresponds to Stage 2 of a procedure. In this position, two ports are effectively closed by being located between seals, namely, port 154*a* which is associated with the outlet of the pump 112 is closed by being located between seals 164*a* and 164*b*, while port 154*e* which is associated with the retention balloon lumen is closed by being located between seals 164*d* and 164*e*. In this second position of the spool 156, two separate flow paths are provided, namely, port 154*b* which is associated with the reservoir 14 and ports 154*c* and 154*d* which are associated with the inlet of the pump 112 are in fluid communication via groove 162*a* due to the location of seals 164*c* and 164*d*, while port 154*f* which is associated with the outlet of the pump 112 and port 154*g* which is associated with the irrigant lumen are in fluid communication via groove 162*b* due to the location of seals 164*e* and 164*f*. Thus, this configuration permits fluid to be pumped from the reservoir to the irrigant lumen, so as to provide irrigation.

Figure 8:
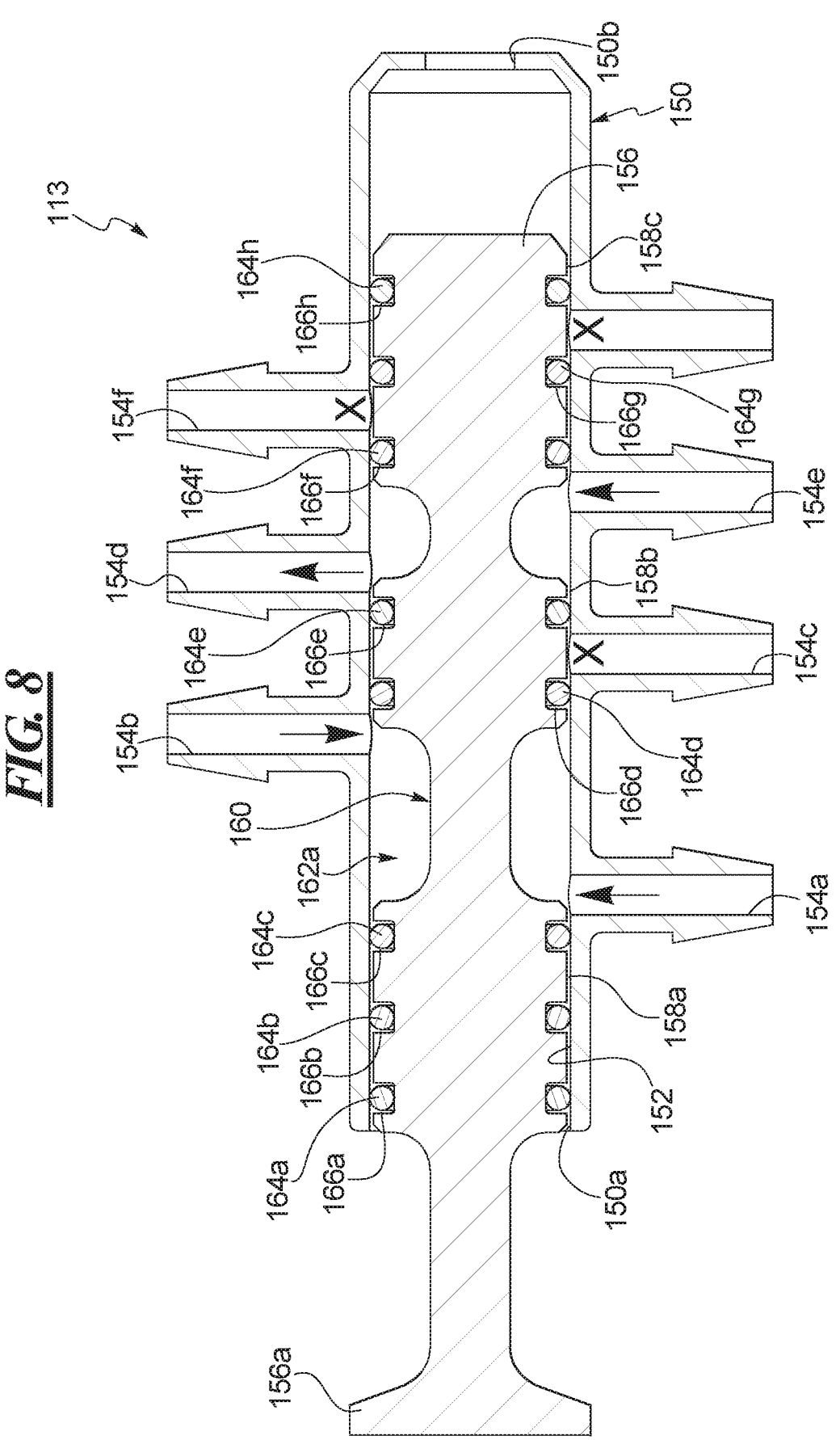
FIG. 8 is a cross-sectional side view of the spool valve of FIG. 2, showing the spool in a Stage 3 position to provide balloon deflation.

Turning to FIG. 8, the spool valve 113 has been moved again and now is in a position that corresponds to Stage 3 of a procedure. In this position, three ports are effectively closed by being located between seals, namely, port 154*c* which is associated with the inlet of the pump 112 is closed by being located between seals 164*d* and 164*e*, while port 154*f* which is associated with the outlet of the pump 112 is closed by being located between seals 164*f* and 164*g*, and port 154*g* which is associated with the irrigant lumen is closed by being located between seals 164*g* and 164*h*. In this third position of the spool 156, two separate flow paths are provided, namely, port 154*a* which is associated with outlet of the pump 112 and port 154*b* which is associated with the reservoir 14 are in fluid communication via groove 162*a* due to the location of seals 164*c* and 164*d*, while port 154*e* which is associated with the retention balloon lumen and port 154*d* which is associated with the inlet of the pump 112 are in fluid communication via groove 162*b* due to the location of seals 164*e* and 164*f*. Thus, this configuration permits fluid to be pumped from the retention balloon lumen to the reservoir to, so as to deflate the retention balloon 24.

In this manner, the spool valve 113 may replace the three solenoid valves, while providing numerous advantages. For example, the spool valve 113 advantageously requires a smaller footprint for the hydraulic control circuit within the base unit 12. Also, a single actuator 115 may be used to move the spool 156, replacing the three solenoids that otherwise are used for actuation of the three solenoid valves. Additionally, the spool valve 113 components may be molded or otherwise constructed of less expensive and lighter weight materials that do not corrode, such as polymer materials for the spool 156 and valve body 150, and polymer or rubber materials for the seals 164*a*-164*h* disposed between the spool 156 and the bore 152 of the valve body 150.

Indeed, the description of the Stages and general operation of the device 10 of the present disclosure proceeds in a manner somewhat similar to that which is described and shown with respect to FIGS. 1-14 of International Patent Application No. PCT/US17/41205. However, the single spool valve 113 and single actuator 115 replace the three solenoid valves. The spool valve 113 uses three positions to provide a hydraulic control circuit having the fluid flows similar to those discussed in International Patent Application No. PCT/US17/41205 for Stages 1, 2 and 3 of operation of the device 10. The ports 154a-154g would be connected to the other components, including fluid connection of port 154a to an outlet of the pump 112; fluid connection of port 154b to the reservoir 14; fluid connection of port 154c to an inlet of the pump 112; fluid connection of port 154d to the inlet of the pump 112; fluid connection of port 154e to the retention balloon 154; fluid connection of port 154f to the outlet of the pump 112; and fluid connection of port 154g to an irrigant lumen of the tube 16.

Accordingly, this disclosure provides a trans-anal irrigation device 10 having a spool valve 113, with the device 10 including a pump 112, an irrigation fluid reservoir 14 in fluid communication with the pump 112, a rectal catheter 20 having a retention balloon 24 and an irrigant passage or main passage through the rectal catheter 20. The device 10 includes fluid tubing having at least two lumens, a first lumen providing fluid communication between the pump 112 and the retention balloon 24, and a second lumen providing fluid communication between the pump 112 and the irrigant passage. The spool valve 113 is part of a hydraulic control circuit including a spool valve 113 having a spool 152 that is movable by an actuator 115.

Figure 5:
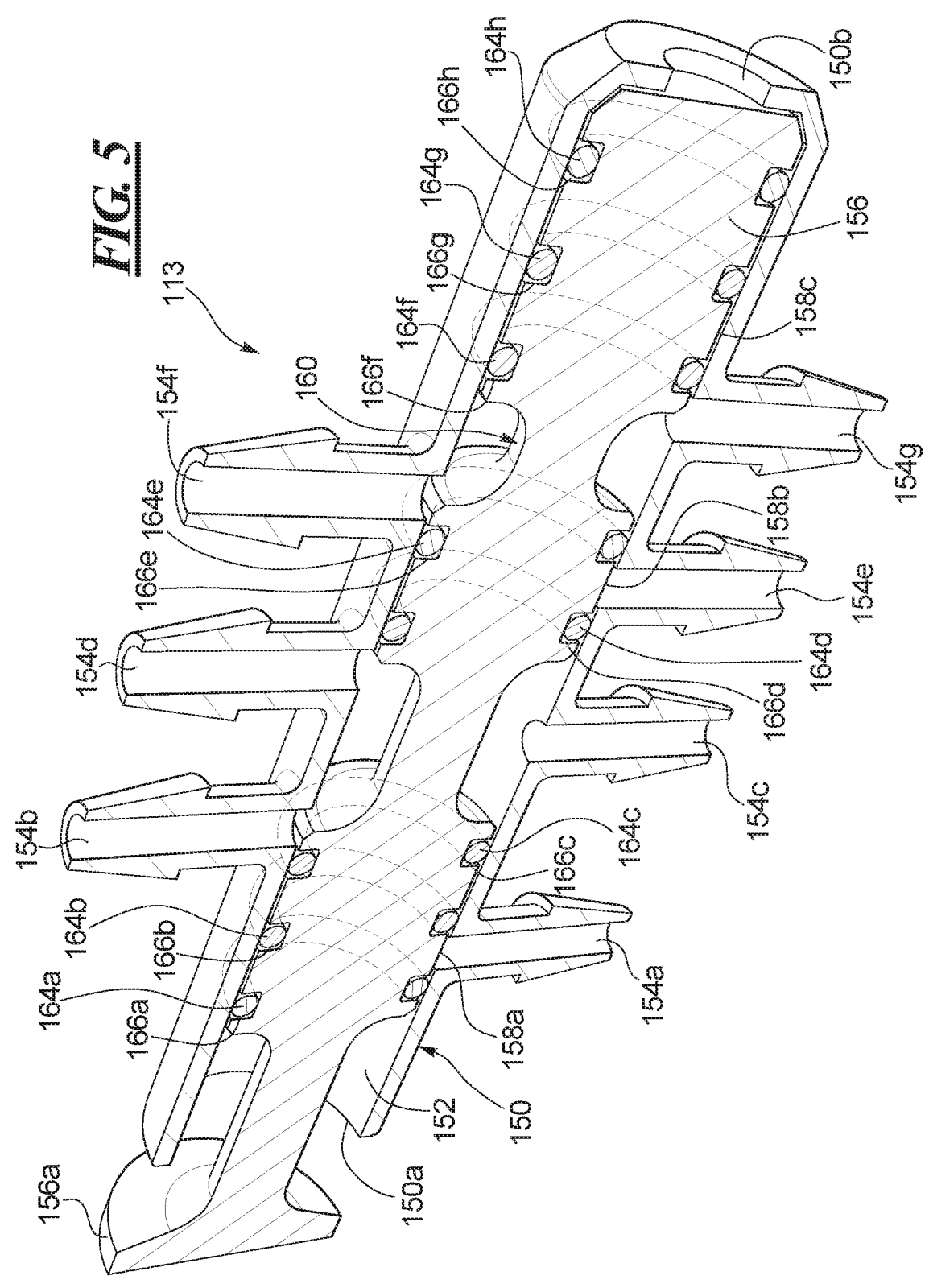
FIG. 5 is a cross-sectional perspective view of the spool valve of FIG. 2, showing the spool in the bore of the valve body, in the Stage 2 position to provide irrigant.

The spool valve 113 includes a valve body 150 having an elongated bore 152, and a plurality of ports 154a-154g spaced apart along and in fluid communication the bore 152. The spool 156 further includes a plurality of lands 158a-158c, separated by a plurality of grooves 166a-166h. The spool 156 further includes seals 164a-164h extending outward from the lands 158a-158c and sealingly engaging the elongated bore 152 of the valve body. The plurality of ports 154-154g and plurality of seals 164a-164h and grooves 166a-166 are arranged for selectively directing flow alternatively from the reservoir 14 to the retention balloon 24, for Stage 1 of a procedure and as shown in FIG. 6, from the reservoir 14 to the irrigant passage in the catheter 20, for Stage 2 of a procedure and as shown in FIGS. 5 and 7, or from the retention balloon 24 to the reservoir 14, for Stage 3 of a procedure and as shown in FIG. 8, each of which is based on the position of the spool 156 within the valve body 150.

Thus, it will be appreciated that with the trans-anal irrigation device 10, a first port 154a of the plurality of ports is associated with and fluidly connected to an outlet of the pump, a second port 154b of the plurality of ports is associated with and fluidly connected to the reservoir, a third port 154c of the plurality of ports is associated with and fluidly connected to an inlet of the pump, a fourth port 154d of the plurality of ports is associated with and fluidly connected to an inlet of the pump, a fifth port 154e of the plurality of ports is associated with and fluidly connected to the retention balloon, a sixth port 154f of the plurality of ports is associated with and fluidly connected to the outlet of the pump, and a seventh port 154g of the plurality of ports is associated with and fluidly connected to an irrigant lumen that is in fluid communication with the irrigant passage through the rectal catheter. The spool 156 of the spool valve 113 is movable linearly to at least three different hydraulic control positions.

It will be appreciated that the spool valve 113 may be used to perform a method of establishing fluid paths through a spool valve 113 in a hydraulic control circuit of a trans-anal irrigation device 10, wherein the spool valve 113 comprises a valve body 150 having an elongated bore 152 and a plurality of ports 154a-154g spaced apart along and in fluid communication with the bore 152, and a spool 156 that is movable within the bore 152, and wherein the plurality of ports 154a-154g further include a first port 154a associated with a pump outlet, a second port 154b associated with a reservoir, a third port 154c associated with a pump inlet, a fourth port 154d associated with a pump inlet, a fifth port 154e associated with a retention balloon lumen, a sixth port 154f associated with a pump outlet, and a seventh port 154g associated with an irrigant lumen, with the method including at least three steps that correspond to the aforementioned Stages 1, 2 and 3.

Thus, the at least three steps include: (1) moving the spool 156 to a first position within the bore 152 of the valve body 150 wherein the second port 154b is in fluid communication with the third port 154c and the fifth port 154e is in fluid communication with the sixth port 154f, so as to establish fluid paths through the spool valve 113 from the reservoir 14 to the pump inlet and from the pump outlet to the retention balloon lumen, such as to perform Stage 1 of an anal-irrigation procedure, as shown in FIG. 6; (2) moving the spool to a second position within the bore 152 of the valve body 150 wherein the second port 154b is in fluid communication with the third and fourth ports 154c, 154d and the sixth port 154f is in fluid communication with the seventh port 154g, so as to establish fluid paths through the spool valve 113 from the reservoir 14 to the pump inlet and from the pump outlet to the irrigant lumen, such as to perform Stage 2 of an anal-irrigation procedure, as shown in FIGS. 5 and 7; and (3) moving the spool 156 to a third position within the bore 152 of the valve body 150 wherein the first port 154a is in fluid communication with the second port 154b and the fourth port 154d is in fluid communication with the fifth port 154e, so as to establish fluid paths through the spool valve 113 from the retention balloon lumen to the pump inlet and from the pump outlet to the reservoir 14, such as to perform Stage 3 of an anal-irrigation procedure, as shown in FIG. 8.

The method may further include use of an actuator 115 that may be connected to the proximal end 156a of the spool 156, and which moves the spool 156 between the first, second and third positions. The method also may include wherein the spool valve 113 further includes a plurality of lands 158a-158c and a plurality of seals 164a-164h extending radially outward from the lands 158a-158c and sealingly engaging the spool 156 and the bore 152 of the valve body 150. The plurality of ports 154a-154g and plurality of seals 164a-164h are arranged to selectively direct flow through the spool valve 113 based on the position of the spool 156.

It should be understood that various changes and modifications to the presently preferred embodiments described herein will be apparent to those skilled in the art. Such changes and modifications can be made without departing from the spirit and scope of the invention disclosed herein.

The invention claimed is:

1. A method of establishing fluid paths through a spool valve in a hydraulic control circuit of a trans-anal irrigation device, wherein the trans-anal irrigation device includes a pump with at least one pump inlet and at least one pump outlet, wherein the spool valve comprises a valve body having an elongated bore and a plurality of ports spaced apart along and in fluid communication with the bore, and a spool that is movable within the bore, and wherein the plurality of ports further comprises a first port associated with the at least one pump outlet, a second port associated with a reservoir, a third port associated with the at least one pump inlet, a fourth port associated with the at least one pump inlet, a fifth port associated with a retention balloon lumen, a sixth port associated with the at least one pump outlet, and a seventh port associated with an irrigant lumen; with the method comprising the steps of:

moving the spool to a first position within the bore of the valve body wherein the second port is in fluid communication with the third port and the fifth port is in fluid communication with the sixth port, so as to establish fluid paths through the spool valve from the reservoir to the at least one pump inlet and from the at least one pump outlet to the retention balloon lumen;

moving the spool to a second position within the bore of the valve body wherein the second port is in fluid communication with the third and fourth ports and the sixth port is in fluid communication with the seventh port, so as to establish fluid paths through the spool valve from the reservoir to the at least one pump inlet and from the at least one pump outlet to the irrigant lumen; and moving the spool to a third position within the bore of the valve body wherein the first port is in fluid communication with the second port and the fourth port is in fluid communication with the fifth port, so as to establish fluid paths through the spool valve from the retention balloon lumen to the at least one pump inlet and from the at least one pump outlet to the reservoir.

2. The method of claim 1, further comprising an actuator that moves the spool between the first, second, and third positions.

3. The method of claim 2, wherein the actuator moves the spool linearly.

4. The method of claim 1, wherein the spool valve further comprises a plurality of lands and a plurality of seals extending radially outward from the plurality of lands and sealingly engaging the spool and the bore of the valve body.

5. The method of claim 4, wherein the plurality of ports and the plurality of seals are arranged to selectively direct flow through the spool valve based on the position of the spool.

6. The method of claim 4, wherein the plurality of seals is constructed of polymer or rubber materials.

7. The method of claim 4, wherein the plurality of seals are constructed as O-rings.

8. The method of claim 4, wherein the plurality of lands extend radially outward from a central stem of the spool.

9. The method of claim 8, wherein the plurality of lands further comprise channels that receive the plurality of seals.

10. The method of claim 1, wherein the retention balloon lumen is in fluid communication with a retention balloon.

11. The method of claim 10, wherein the retention balloon is attached to a rectal catheter.

12. The method of claim 11, wherein the retention balloon is attached to an exterior of the rectal catheter.

13. The method of claim 1, wherein the spool and the valve body are constructed of polymer materials.

* * * * *